United States Patent [19]

Rogel et al.

[11] 4,268,791
[45] May 19, 1981

[54] DUAL TRACE AUTOMATIC EDDY CURRENT DETECTION SYSTEM FOR MULTILAYER STRUCTURES

[75] Inventors: Albert P. Rogel, Rancho Cordova; Joseph J. Scalese, Loomis, both of Calif.

[73] Assignee: The United States of America as represented by the Secretary of the Air Force, Washington, D.C.

[21] Appl. No.: 968,042

[22] Filed: Dec. 8, 1978

[51] Int. Cl.³ .......................................... G01V 33/12
[52] U.S. Cl. .................................... 324/238; 324/219
[58] Field of Search ...................... 324/227, 228–230, 324/237, 238, 239, 240, 219–221, 234, 208

[56] References Cited

U.S. PATENT DOCUMENTS

| | | | |
|---|---|---|---|
| 3,056,081 | 9/1962 | Hochschild | 324/238 |
| 3,401,332 | 9/1968 | McClurg et al. | 324/227 |
| 3,538,433 | 11/1970 | Wood et al. | 324/227 |
| 3,718,855 | 2/1973 | Rogel et al. | 324/202 |
| 3,737,764 | 6/1973 | Dufayet | 324/237 |
| 4,083,002 | 4/1978 | Allport | 324/227 |
| 4,117,403 | 9/1978 | Forster et al. | 324/240 |

*Primary Examiner*—Gerard R. Strecker
*Attorney, Agent, or Firm*—Donald J. Singer; Willard Matthews, Jr.

[57] ABSTRACT

An automatic eddy current probe is revolved in a hole to be inspected, the output of the probe is divided to provide two signals to a recorder, a filtered signal will indicate the presence or absence of a flaw, a non filtered signal indicates probe position, this is particularly valuable when scanning through several structural layers.

3 Claims, 3 Drawing Figures

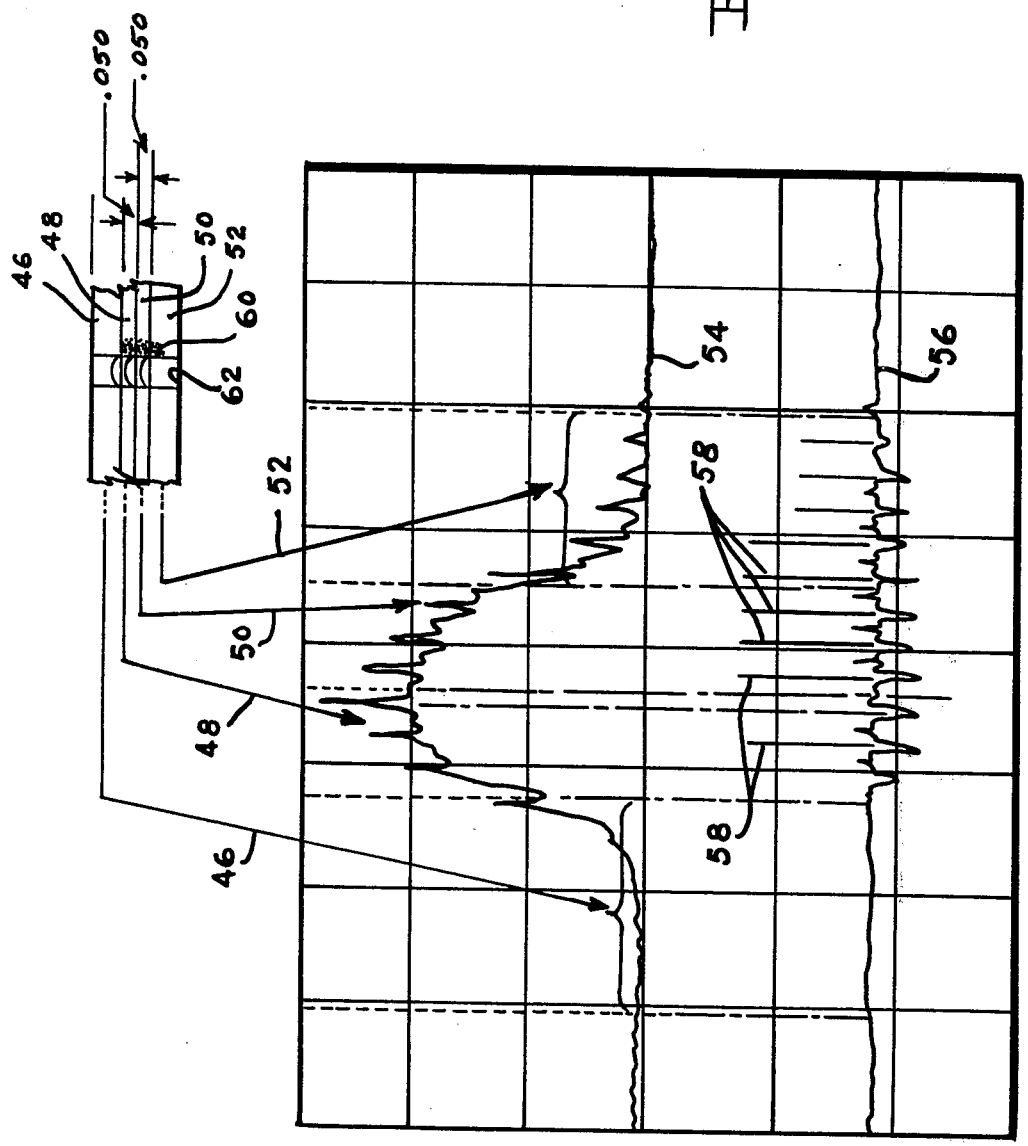

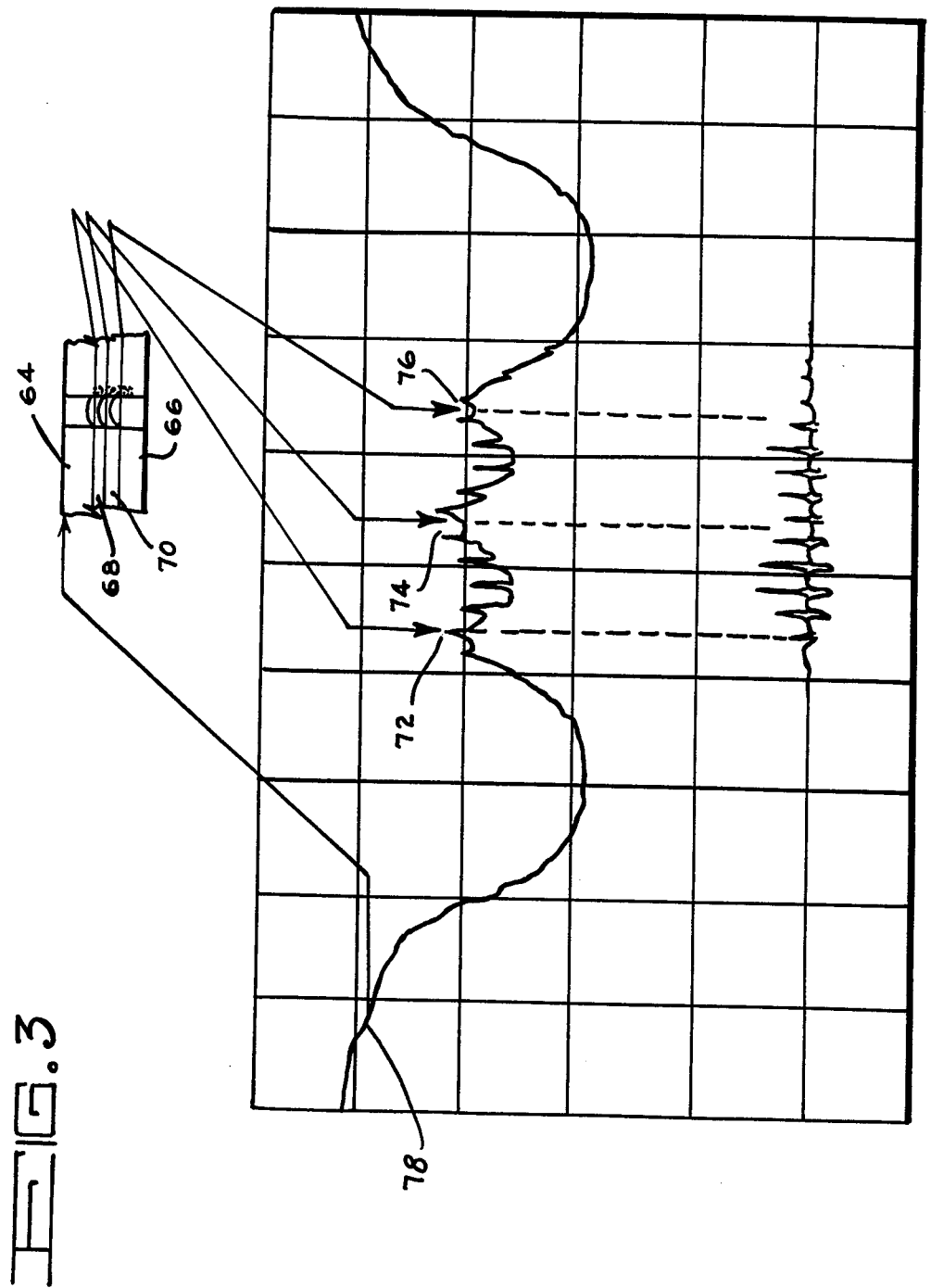

DUAL TRACE AUTOMATIC EDDY CURRENT DETECTION SYSTEM FOR MULTILAYER STRUCTURES

STATEMENT OF GOVERNMENT INTEREST

The invention described herein may be manufactured and used by or for the Government for governmental purposes without the payment of any royalty thereon.

BACKGROUND OF THE INVENTION

This invention relates generally to nondestructive testing and more particularly to an automatic eddy current inspection system having a dual trace output.

Eddy current inspections systems are known in the art and an automatic system is shown in U.S. Pat. No. 3,718,855 granted to us on Feb. 27, 1973. The invention presented herein is an improvement over our known system for the inspection of fastener holes.

When inspecting fastener holes there are many instances where the eddy current probe will pass through multiple layers of material. Although our known system will indicate a flaw in the material, it will also indicate the separation between layers of material. There is currently no known means for distinguishing between a flaw and the separation of layers of inspectable material. Further, there are times when uninspectable material may separate layers which need positive identification. Also, there is a need to be able to determine the orientation of flaws or cracks. Some cracks are radial which others are circumferential. Other flaws may be of the exfoliation type. Presently the determinations of type and size must be made visually with a separate process once it has been discovered.

In fastener hole inspection it is of significant importance to the structural engineer that he know the type and location of the defect. The corrective action required will depend in part upon the particular structural member affected since certain structural members are inherently more critical than others and require immediate attention to prevent disastrous failures.

SUMMARY OF THE INVENTION

The invention utilizes an eddy current detecting system with two channels for inspecting metal flaws, cracks or other discontinuities, initiating in fastener (bolt or rivet) holes, in multi-layered structures. The system includes a motorized scanner with power supply containing an eddy current probe, and recording equipment.

The eddy current probe assembly, is automatically revolved in a fastener hole and flaws are indicated on an eddy current instrument, cathode ray tube, or recorder. One eddy current signal is detected and divided. Two signals are then recorded on a dual trace recorder. One signal is a filtered signal which has long been used to indicate whether or not a flaw is present. The second signal indicates the probe position while scanning through a plurality of structural layers. The result is achieved by a continuing change in the contour pattern of the second signal which is an unfiltered trace, or better described as a raw signal.

In operation, a series of peaks of valleys are recorded while scanning a fastener hole of a multi-layered structure. The interface is clearly defined between each structural member. It is thus possible to pinpoint the area within a multi layered structure when a flaw indication is recorded with the dual trace system.

The invention is particularly adaptable for use with multi-layer structures and provides an eddy current detection system which has field results of extreme reliability. The results of the system when combined with basic engineering data regarding the structure provide the inspector all the information needed to make decisions regarding corrective action.

It is therefore an object of the invention to provide a new and improved automatic eddy current inspection system.

It is another object of the invention to provide a new and improved automatic eddy current inspection system that has as an output more reliable information then any known existing system.

It is a further object of the invention to provide a new and improved eddy current inspection system that is adaptable to be used in multi-layered structures.

It is still another object of the invention to provide a new and improved automatic eddy current inspection that simultaneously provides information regarding a flaw and its exact location.

It is still a further object of the invention to provide a new and improved non destructive inspection system that allows valid repeatable inspections without interference from structural interfaces.

It is another object of the invention to provide a new and improved non destructive, eddy current inspection system that is easily maintained, simple to operate and provides accurate test results.

These and other advantages, features and objects of the invention will become more apparent from the following description taken in connection with the illustrative embodiment in the accompanying drawing.

DESCRIPTION OF THE DRAWING

FIG. 2 is a graphic representation of the output of the invention.

FIG. 3 is a graphic representation of the output of the invention using thicker materials than shown in FIG. 2.

DESCRIPTION OF THE PREFERRED EMBODIMENT

Figure 1:
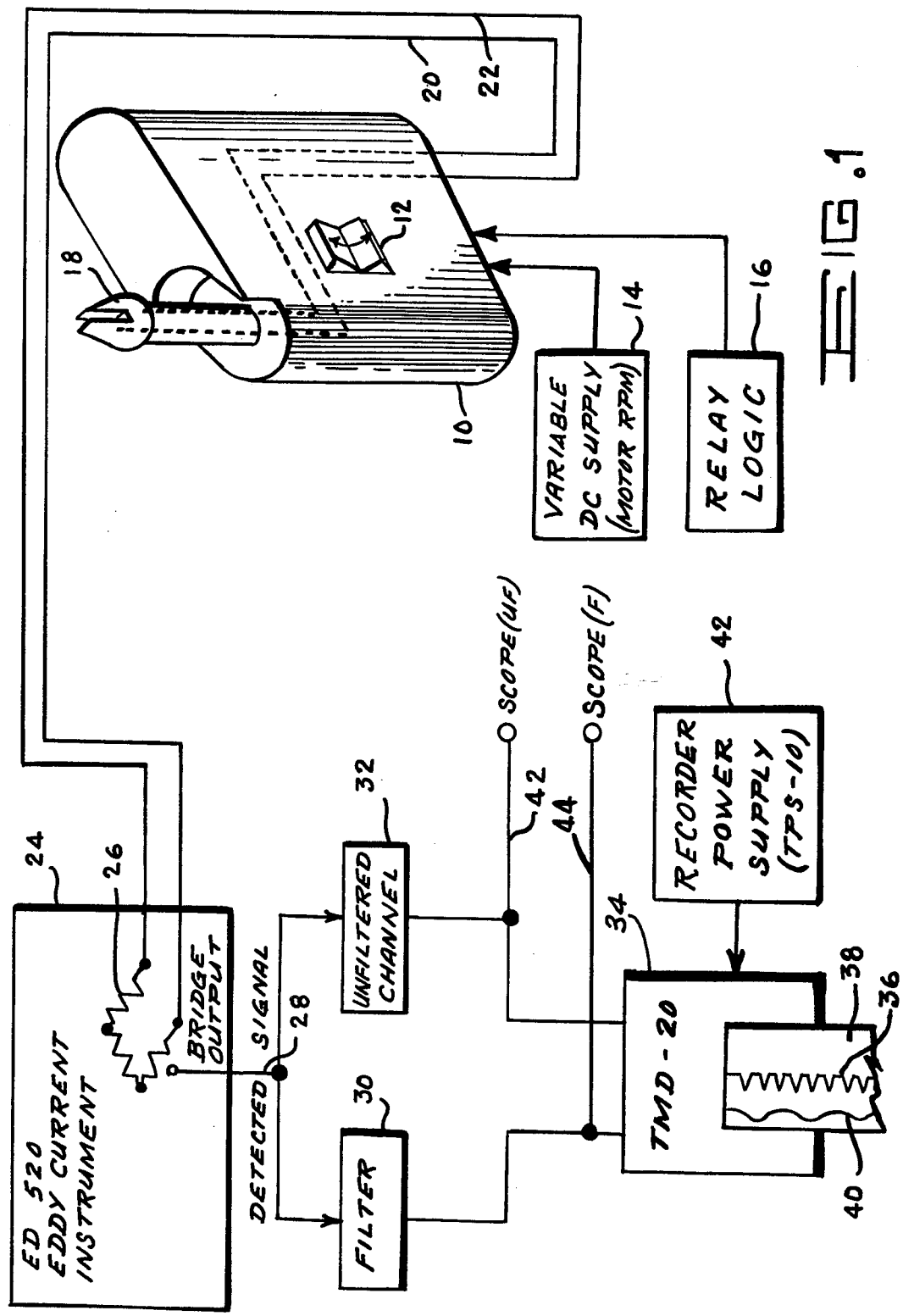
FIG. 1 is a schematic representation of the invention.

Referring now to FIG. 1, a motorized eddy current scanner is shown at 10. The scanner is controlled by a rocker switch 12 which controlls the variable DC power supply 14 and relay logic 16. The eddy current probe 18 is connected via lines 20, 22 to the eddy current control instrument 24. A typical control instrument is the Maguaflux ED520 manufactured by Magnaflux Corporation of Chicago, Ill., although other similar devices might be used. The control instrument contains a bridge circuit 26 which is the conventional manner of drawing output from the eddy current probe.

The bridge output 28 is divided and the detected signal is sent through filtered circuit 30 passing frequencies in the order of ten cycles per second in a conventional manner to provide an output indicating the presence or absence of a flaw in the material tested. The signal is also sent to circuit 32 where it passes unfiltered, directly to the recorder 34. The unfiltered signal produces a trace 36 on the chart paper 38 indicating the various layers of material by the intersitial spacing. Trace 40 follows from circuit 30 and indicates the condition of the layer that is being inspected. The recorder is powered by supply 42.

Alternatively or in addition, the signals from circuits 30 and 32 may be sent via lines 42, 44 to a cathode ray tube where the dual trace would be observed but not recorded.

FIG. 2 shows the output of a dual trace recorder system investigating an aircraft wheel well assembly including the bracket 46, pan 48, skin 50 and frame 52. Unfiltered data is shown on tracing 54 which clearly delineates the layers being inspected. Filtered data is shown on trace 56 which indicates via spikes 58 that there is a flaw shown at 60 in the fastener hole 62. Interpretation of the tracing by an experienced operator will show the exact location and nature of the flaw.

Concerning FIG. 3, the output of the dual trace recorder system is of four-layered assembly from the F-104 fuselage main frame longeron area. End members 64, 66 are approximately 5/16 inch thick, while the two intermediate members 68, 70 are 0.125 inch thick. The trace using thicker materials more clearly defines the interface between layers. Points 72, 74 and 76 on trace 78 show the interface for each structural member.

Although the invention has been described with reference to a particular embodiment, it will be understood to those skilled in the art that the invention is capable of a variety of alternative embodiments within the spirit and scope of the appended claims.

We claim:

1. An automatic eddy current flaw detection system for inspecting fastener holes in multi-layered structures comprising a motorized scanner having a rotatable probe for insertion into said fastener holes, said probe generating eddy current signals, an eddy current detection system receiving said eddy current signals, recording means for recording the output of the eddy current detection system, a first circuit including filter means, connected between the eddy current detection system and the recording means for providing a filtered detected signal for recording in the recording means whereby flaws in said multilayered structure will be indicated and a second circuit, connected between the edddy current detection system and the recording means which allows the detected signal to pass unfiltered to the recording means, whereby the boundaries between each layer in the multilayered structure will be defined, said recording means presenting the filtered and unfiltered signals in time coincident juxtaposition.

2. An automatic eddy current flaw detection system adapted for determining flaws in multi-layered structures according to claim 1 wherein the means for recording the output of the detection system is a dual trace chart recorder.

3. An automatic eddy current flaw detection system adapted for determining flaws in multi-layered structures according to claim 2 wherein the output of the detection system is observed on a dual trace cathode ray tube.

* * * * *